United States Patent [19]

Esnouf

[11] Patent Number: 5,500,349

[45] Date of Patent: Mar. 19, 1996

[54] BLOOD-COAGULATION FACTOR XIIA β MONOCLONAL ANTIBODY AND IMMUNOASSAY

[75] Inventor: Michael P. Esnouf, Combe, England

[73] Assignee: Coagen Limited, Oxford, United Kingdom

[21] Appl. No.: 153,800

[22] Filed: Nov. 17, 1993

Related U.S. Application Data

[63] Continuation of Ser. No. 730,846, Sep. 17, 1991, abandoned.

[30] Foreign Application Priority Data

Jan. 27, 1989 [GB] United Kingdom ............... 8901859

[51] Int. Cl.$^6$ .................. G01N 33/53; G01N 33/68; C12N 5/12; C07K 16/36
[52] U.S. Cl. .................. 435/7.4; 435/7.1; 435/70.21; 435/240.27; 435/975; 530/388.25; 530/388.26; 530/391.3
[58] Field of Search .................. 435/7.1, 7.4, 7.91, 435/7.92, 70.21, 172.2, 240.27, 975; 530/387.1, 388.1, 388.25, 388.26, 391.1, 391.3

[56] References Cited

U.S. PATENT DOCUMENTS 4,963,657 10/1990 Pixley ........................ 530/387

OTHER PUBLICATIONS

Fujikawa, K. and McMullen, B. A. J. Biol. Chem. 258:10924–10933 (1983).
McMullen, B. A. and Fujikawa, K. J. Biol Chem 260:5328–5341 (1985).
Cool, D. E. et al J. Biol Chem 260:13666–13676 (1985).

*Primary Examiner*—Margaret Parr
*Assistant Examiner*—Phillip Gambel
*Attorney, Agent, or Firm*—Pennie & Edmonds

[57] ABSTRACT

A monoclonal antibody which binds to Factor βXII and which shows substantially no binding to Factor XII. This antibody may be used in immunoassays to measure Factor βXIIa levels in blood, for example for studies of blood coagulation systems and of thrombotic disorders.

20 Claims, 3 Drawing Sheets

BLOOD-COAGULATION FACTOR XIIA β MONOCLONAL ANTIBODY AND IMMUNOASSAY

The present application is a continuation of U.S. patent application Ser. No. 07/730,846, filed Sep. 17, 1991, now abandoned which is a national phase U.S. patent application of International Application PCT/GB90/00129, filed Jan. 29, 1990, which claims priority to Great Britain Application No. 8901859.2, filed on Jan. 27, 1989, each of which is incorporated by reference herein in its entirety.

The present invention relates to an immunoassay and to reagents for such an assay. It relates in particular to blood coagulation Factor XII and activated forms thereof, Factor XIIa.

Factor XII is an inactive zymogen present in normal blood. Factor XII is readily converted, in the presence of kallikrein, high molecular weight kininogen and a negatively charged surface into a two chain form that is enzymatically active. This 80-KDa serine proteinase, often called Factor αXIIa, has a 52-KDa heavy chain linked by a disulphide bond to a 28-KDa light chain. Proteolysis of this factor releases a 40-KDa peptide from the heavy chain, and results in a product, Factor βXIIa, that retains serine protease activity, but in which the 28-KDa chain of Factor αXIIa is disulphide-linked to a small peptide fragment derived from the former 52-KDa heavy chain. In many cases the small peptide fragment has a molecular weight of 2000-Da, but fragments of different size have been observed, for example, 800-Da and 3000-d fragments.

The term "Factor XIIa", abbreviated to "XIIa" is used herein to denote any form of activated Factor XII, that is to say, any derivative of Factor XII having serine proteinase activity. It includes any form of XIIa produced from Factor XII in vitro and any form occurring in vivo and obtainable from natural sources. It further includes any analogue of a naturally-occurring protein that has a modified amino acid sequence, for example, one or more so-called "conservative" changes to the amino acid sequence, that is to say, changes (additions, removals or substitutions) that do not affect the properties of the molecule, in particular the immunogenic and enzymatic properties. The term includes any synthetic copy and any synthetic analogue of a naturally occurring Factor XIIa, whether produced by chemical synthesis or by recombinant DNA technology. It includes any form of αXIIa and any form of βXIIa. The terms "βXIIa" and "Factor βXIIa", and "αXIIa" and "Factor αXIIa" are used analogously herein to denote any form of such a molecule.

The amino acid sequence of a form of Factor βXIIa having a 2000-Da peptide fragment has been described (K. Fujikawa & B. A. McMullen, J. Biol. Chem. 258, 10924–10933, 1983), and speculations have been made as to its tertiary structure (D. E. Cool et al., J. Biol. Chem. 260, 13666–13676, 1985). The cleavage sites of this form of βXIIa have been defined further by Cool et al. (J. Biol. Chem. 262, 13662–13672, 1987): αXIIa is stated to be produced from XII by cleavage between $Arg^{353}$-$Val^{354}$, and βXIIa is produced from αXIIa by cleavage between $Arg^{334}$-$Asn^{335}$, $Arg^{343}$-$Leu^{344}$ and $Arg^{353}$-$Val^{354}$, resulting in two polypeptide chains of 9 and 243 residues respectively.

Although the present invention is particularly concerned with human Factor XIIa it is not limited to the human protein or to a XIIa protein having any specific amino acid sequence (see Fujikawa & McMullen above).

It is known that elevated blood levels of cholesterol, Low Density Lipoprotein (LDL) and Apolipoprotein B are positively correlated with the long term mortality risk from Ischaemic Heart Disease (IHD) and Acute Myocardial Infarction (AMI). Similar positive correlations are found with lowered blood levels of High Density Lipoprotein (HDL) and Apolipoprotein A1.

None of these parameters, however, is usefully predictive of the risk of AMI in individuals. Meade et al. from Northwick Park Hospital (Meade et al. Lancet (i) 1050–4; Meade. Haemostasis 1983, 13, 178–85; Meade et al. Lancet 1986, (ii) 533–7) and Kannel, Wolf, Castelli & Agostino of the Framingham Study (Kannel et al. J.A.M.A. 1987, 258(9), 1183–6) have shown that, under carefully controlled conditions, measurements of fibrinogen and Factor VII coagulant activity can predict the likelihood of AMI better than can various lipid measurements. Factor VII itself is a single chain protein having low activity but it can be converted to a two chain form, Factor VIIa, which more active. Substances that can activate Factor VII to VIIa include Factor Xa, Factor IXa, Factor XIIa, thrombin.

As indicated above, Factor VII activity has been shown under carefully controlled conditions to be useful in predicting the likelihood of AMI in individuals. However, currently available methods of measuring Factor VII activity are subject to large variations. In particular venepuncture, the method generally used to obtain blood samples, releases variable amounts of tissue factor which, as mentioned above, is involved in one method of activation of Factor VII. Accordingly the use of Factor VII activity in predicting AMI is not sufficiently reliable for general use.

The present invention is based on the observation that an increased level of lipids in the diet increases Factor VII activity by increasing the steady state concentration of Factor XIIa, for example βXIIa. That is to say, Factor XIIa, for example βXIIa, is a link between hyperlipidaemia and Factor VII.

Accordingly, it is proposed to use measurements of levels of Factor XIIa, for example βXIIa, in plasma to predict the likelihood of heart disease, in particular, ischaemic heart disease and acute myocardial infarction (AMI) in individuals, in analogy to the use of Factor VII activity, but avoiding the disadvantage of tissue factor activation that occurs when samples of Factor VII are obtained.

Before the present invention, however, there was not a Factor XIIa assay that was rapid, selective, sufficiently sensitive to detect accurately XIIa at levels below about 10 ng/ml, and that could be automated readily for large scale use.

The method used previously to determine Factor XIIa is an enzyme assay in which a chromogenic substrate is hydrolyzed. As well as the lack of sensitivity mentioned above, a further disadvantage with this assay is that the chromogenic substrate is hydrolyzed by a number of other substances that occur in plasma, including Factor Xa, kallikrein and thrombin. It is necessary, therefore, to estimate and make allowances for this hydrolysis, which will inevitably introduce inaccuracies, particularly at low XIIa levels. This assay cannot be regarded as giving accurate results at levels of XIIa below about 10 ng/ml.

Approaches to improving the assay of XIIa and other clotting factors have involved the provision of improved chromogenic substrates see, for example, EP 78764-B and EP 285000-A.

Other, non-chromogenic types of assay have been proposed for blood clotting factors, for example, WO-8606489-A discloses the use of surface-bound fibrinogen and labelled fibrinogen. Immunoassays have also been proposed, for example, EP-325723-A discloses in general terms the use of a microparticle carrier sensitized with a monoclonal antibody to a blood clotting factor.

J62065693-A discloses a monoclonal anti-human blood coagulation Factor XI antibody. This antibody is stated to have strong affinity to the active type factor XI as well as to the blood coagulation factor XI itself. The monoclonal antibody may be used for the determination of human blood coagulation Factor XI and the active type of Factor XI by various forms of immunoassay.

There has been described a monoclonal antibody that can recognize Factor XII and Factor αXIIa, but that does not recognize Factor βXIIa (E. J. Small et al., Blood, 65, 202–210, 1985). This is not surprising, because the authors found that the antibody was directed to the 40-KDa fragment that is released from Factor αXIIa when it is converted into Factor βXIIa, that is to say, the antibody was directed to an antigenic determinant that is part of the Factor XII and Factor αXIIa molecules but which physically does not exist in the βXIIa molecule.

The present invention provides a monoclonal antibody that binds to Factor βXIIa and that shows substantially no binding to Factor XII. A monoclonal antibody of the invention may bind to Factor βXIIa specifically or may also bind to Factor αXIIa.

It is surprising that, in contrast to J6206593-A and Small et al., the monoclonal antibodies of the present invention are able to recognise activated Factor XII and to discriminate between activated XII and the zymogen Factor XII itself.

The present invention provides a method of detecting and/or determining Factor XIIa or βXIIa in a sample, which comprises subjecting the sample to a qualitative or quantitative immunoassay which comprises the interaction between an antigen and an antibody and the detection and/or determination of any resulting antibody-antigen complex, characterized in that the antibody is a monoclonal antibody of the present invention. Factor βXIIa is generally used as the standard for such an assay.

The present invention also provides a method of carrying out an immunoassay for an antigen in a sample of fluid, which assay comprises an interaction between the antigen and an antibody that binds thereto, and determining the amount of antigen present in the sample by reference to results obtained using pre-determined amounts of a known antigen, characterised in that the antibody is a monoclonal antibody of the invention and the known antigen is Factor βXIIa.

An immunoassay of the invention provides a rapid method of determination that can readily be used on automated equipment for large scale use. The assay is also accurate and sensitive, and can be used to detect levels of XIIa and βXIIa well below the effective lower limit of 10 ng/ml for the previously used chromogenic assay.

The antibodies and immunoassays of the present invention are, accordingly, useful for assaying Factor XIIa or βXIIa, particularly when a large number of assays are to be carried out, either in a research laboratory or in a clinical laboratory. An antibody and an immunoassay of the invention are particularly suitable for use in epidemiological studies to provide data that can be used in analogy to the Factor VII data discussed above in an assessment of the risk of heart disease, in particular, ischaemic heart disease and/or of acute myocardial infarction in an individual.

The present invention accordingly provides a method wherein an immunoassay of the invention is carried out on a sample of plasma obtained from a human subject and wherein, to determine the susceptibility of the subject to heart disease, the result obtained for the level of the antigen in the sample assayed is compared with the results obtained in a large-scale investigation which correlates the level of that antigen with susceptibility to heart disease. The individual assays and large-scale investigation preferably carried out using the same antibody. It is generally preferable also to use the same immunoassay.

Monoclonal antibodies and immunoassays of the present invention may also be used in studies of coagulation systems and of thrombotic disorders.

If it is desired to know whether a particular monoclonal antibody is βXIIa-specific or if it also binds to αXIIa, this may be done by carrying out an immunoassay on the antibody using Factor αXIIa as an antigen. The immunoassay may be qualitative or quantitative, as desired, but it is generally preferable to use a liquid phase assay rather than a solid phase assay. In many cases, however, it is considered not to be essential to determine specificity towards αXIIa, since it is believed that satisfactory results will be obtained provided that the same antibody is used for all assays that will be compared with each other. (It will be noted that generally the results of an assay of the invention will be determined relative to βXIIa standards, and so may be considered as representing measurement of βXIIa and βXIIa-equivalents.)

The present invention also relates to a peptide that is a fragment of βXIIa that is or that includes at least one antigenic determinant capable of recognising anti-Factor βXIIa. An antigenic fragment of βXIIa may itself be immunogenic or may be too small to be immunogenic, in which case it may be converted into an immunogen, for example, by conjugation to another peptide, for example, as described below. The term "antigenic fragment of βXIIa" as used herein includes both a peptide as defined above and an immunogenic form of such a peptide if it is not itself immunogenic.

Figure 1:
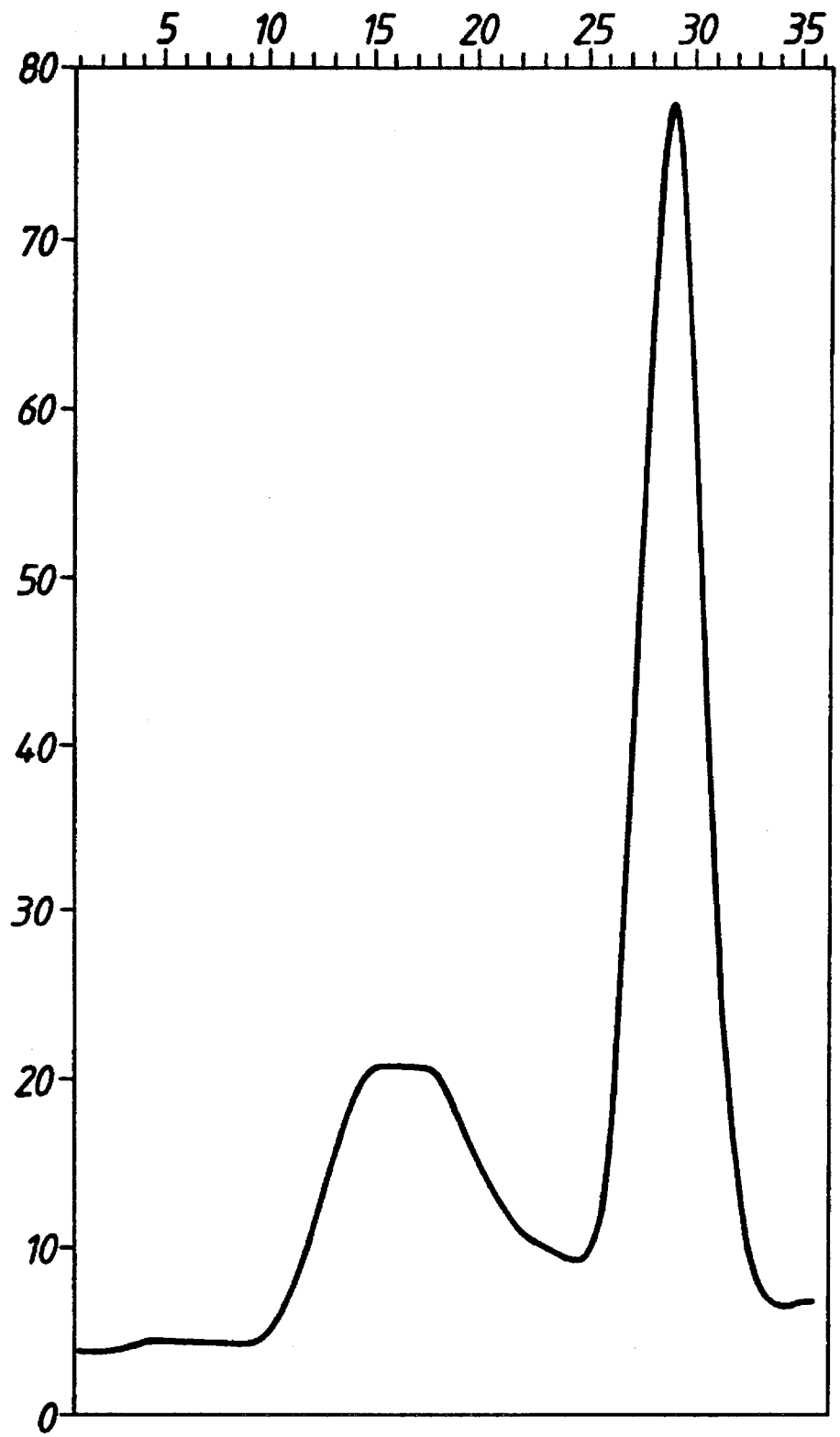
FIG. 1—A plot of absorbance at 280 nm against time for the eluate of the DEAE-"SEPHACEL" column and shows Factor βXIIa in the second peak.

Methods of preparing immunogens are known to those in the art. Any of these methods may be utilised to render immunogenic or to improve the immunogenicity of Factor βXIIa or antigenic fragment thereof.

In essence, all the methods comprise attaching a molecule which may not be antigenic or sufficiently antigenic to a larger protein molecule in order that an immune response or an improved immune response may be obtained on immunization. Protein molecules used as carriers, are, for example, keyhole limpet haemocyanin, bovine serum albumin, bovine thyroglobulin and a purified protein derivative of tuberculin. For example, keyhole limpet haemocyanin (KLH) may be coupled to a cysteine-containing peptide via the cysteine thiol group of the peptide using a bifunctional cross-linking agent, for example, a maleimide reagent, for example, sulfosuccinimidyl-N-maleimido methyl cyclohexane-1-carboxylate, (see E. Isikawa et al. J. Immunoassay 1983, 4, 209). The resultant conjugate may be purified by gel filtration chromatography and lyophilised.

A peptide that does not have an intrinsic thiol group may have a cysteine residue introduced at the N and/or C-terminus. A conjugate may be used to coat a solid phase, for example, wells of a plastics microtitre plate.

Factor βXIIa may be produced by a method which comprises first isolating Factor XII from fresh or freshly frozen plasma, for example, using a combination of ammonium sulphate precipitation and anion exchange chromatography for example, according to the method described by K. Fujikawa and E. W. Davie (Methods in Enzymol, 1981, 80, 198–211). Methods for converting Factor XII to Factor βXIIa and isolating Factor βXIIa from the resulting mixture are described by K. Fujikawa and B. A. McMullen (Journal of Biol. Chem., 1983, 258, 10924–10933) and B. A. McMullen and K. Fujidawa (Journal of Biol. Chem. 1985, 260, 5328). To obtain Factor βXIIa, Factor XII is then generally subjected to limited cleavage, for example, by chemical or enzymatic digestion, for example, using trypsin or a trypsin-like enzyme, generally in a highly diluted form, for example, in a molar ratio of trypsin:Factor XII of 1:500, for example, in a weight ratio trypsin:Factor XII of 1:75 and the cleavage products separated, generally by chromatography.

Some preparations of Factor XII contain a substantial amount of αXIIa, as judged by examination of a reduced sample on SDS-PAGE, when three protein bands with apparent molecular weights of 80, 52 and 28-KDa are observed. Such Factor XII preparations also display amidolytic activity. According to Fujikawa & Davie, Factor XII and αXIIa can be separated using benzamidine-agarose column chromatography. On elution, two peaks are observed, both of which have clotting activity. However, only the second peak has amidolytic activity. Provided that the material applied to the benzamidine-agarose column contained no βXIIa, which may be determined by analysis of a non-reduced SDS-PAGE gel, then the second peak is αXIIa. This can be confirmed by running reduced and non-reduced samples on SDS-PAGE.

An antigenic fragment of βXIIa may be produced by degradation of βXIIa by enzymatic or chemical means. For example the disulphide-linked light chain peptide of βXIIa can be obtained by reduction and carboxymethylation of βXIIa and isolation of the fragment by chromatography (K. Fujikawa and B. A. McMullen Journal of Biol. Chem. 1983, 258, 10924).

Alternatively, an antigenic fragment of βXIIa, if its amino acid sequence is known, may be produced synthetically, as may βXIIa itself. Any of the many known chemical methods of peptide synthesis may be used, especially those utilizing automated apparatus.

An antigenic fragment of βXIIa may be produced using the techniques of recombinant DNA technology, as may βXIIa itself. (Cool et al., 1985 and 1987, loc. cit. have characterised a human blood coagulation factor XII cDNA and gene.) This may be achieved, for example, by construction of a gene, for example, by chemical synthesis or by reverse transcription from the corresponding m-RNA, insertion of the gene into an appropriate vector, for example, a plasmid, for example, pBR 322, insertion of the vector into a host organism, for example, E. coli, and expression of the gene in the host organism. Such procedures are now routine, particularly as vectors, for example, PBR 322 are available commercially. Maniatis et al., Molecular Cloning, Cold Spring Harbor Laboratory, 1982 is a standard work giving details of techniques used in this field. Generally chemical synthesis is preferred for smaller peptides, with recombinant DNA becoming more commercially attractive than chemical synthesis for large peptides.

Unless specified otherwise, the terms "Factor βXIIa" and "βXIIa" as used herein include antigenic fragments of the βXIIa molecule.

Factor βXIIa may be used to produce monoclonal antibodies or polyclonal antisera and these monoclonal antibodies are part of the present invention. As indicated above, a monoclonal antibody of the present invention may be capable of binding to Factor βXIIa (it may be capable of recognizing an antigenic determinant characteristic of βXIIa) and of showing no significant binding to Factor XII (capable of distinguishing between Factor βXIIa and Factor XII), or may be capable of binding to βXIIa and αXIIa, in which case the antibody may recognize antigenic determinants common to Factors βXIIa and αXIIa. Polyclonal antisera bind preferentially to βXIIa.

The term "antibody" as used herein includes any antibody fragment that is capable of binding antigen, for example, Fab and F(ab')$_2$ fragments.

As indicated above, a monoclonal antibody of the present invention shows substantially no binding to Factor XII. For use in immunoassays for diagnostic purposes, the corrected cross-reactivity with Factor XII (see below) should generally be 0.1% or less. For other purposes, for example, for use as an immunoadsorbent, a higher cross-reactivity may be acceptable. A monoclonal antibody of the invention preferably has an affinity for Factor βXIIa of at least $10^{10}M^{-1}$.

A factor to take into consideration in assessing the cross-reactivity of an antibody of the invention with Factor XII is that even "pure" Factor XII preparations are almost inevitably contaminated with small amounts of XIIa (Silverberg and Kaplan, Blood 60, 1982, 64–70). The small amounts of XIIa present are not significant in most circumstances, but when assessing the degree of cross-reaction it is necessary to determine as accurately as possible the amount of XIIa in a Factor XII and then to take this into account to determine the corrected cross-reaction rather than the initially measured, apparent cross reaction. It has been found, for example, that Factor XII preparations may contain in the region of 0.5 to 0.8% XIIa. Taking this value into account, an apparent cross-reaction with Factor XII of 0.5% becomes a corrected cross reaction of less than 0.1%. Unless specified otherwise, the term "cross reaction" is used herein to mean the corrected cross reaction.

The present invention provides a method of producing a monoclonal antibody of the invention, which comprises cultivating a hybridoma cell line capable of producing the antibody in a growth medium and obtaining the antibody from the growth medium.

The present invention further provides a method of producing a hybridoma cell line which produces a monoclonal antibody of the invention, which comprises administering an antigen to an animal to obtain antibody-producing cells, fusing the resulting antibody-producing cells with myeloma cells, and screening the resulting hybridomas for the production of the monoclonal antibody, wherein the antigen is Factor βXIIa or an antigenic fragment thereof.

Methods used to produce monoclonal antibodies are well known, see for example, Methods in Enzymology, H. Van Vunakis and J. J. Longone (Eds) 1981, 72(B) and ibid, 1983 92(E).

Monoclonal antibodies may be produced, for example, by a modification of the method of Kohler and Milstein (G. Kohler and C. Milstein, Nature, 1975, 256, 495): female BALB/C or C57/B10 mice are immunised by intraperitoneal injection of βXIIa or an antigenic fragment of βXIIa, for example, from 10 to 30 μg, generally 20 μg of βXIIa or a corresponding amount of the other antigen. The βXIIa or other antigen is preferably conjugated to another protein molecule, for example, to bovine thyroglobulin or to a purified protein derivative of tuberculin. The conjugation may be carried out, for example, by a carbodiimide method or by using a hetero-bifunctional reagent. The immunogen is generally presented in an adjuvant, preferably complete Freunds adjuvant. This procedure is generally repeated at intervals, generally using the same immunogen in the same dose, for example, at 3 week intervals the mice are boosted with 20 μg of conjugated βXIIa in complete Freunds adjuvant until suitable response levels are observed. A pre-fusion boost is preferably given prior to sacrifice, for example, intravenously 3 days prior to sacrifice. The antibody response is monitored, for example, by RIA antisera curve analysis using $^{125}$I-radiolabelled βXIIa or other βXIIa antigen prepared by the chloramine-T method (P. J. McConahey and F. J. Dixon, Int. Arch. Allergy Appl. Immunol, 1966, 29, 185). Purity is confirmed, for example, by using autoradiography, for example, of SDS-PAGE gels run under reducing conditions.

Immune mouse spleen cells are then fused with myeloma cells, for example, NSO mouse myeloma cells, for example in the presence of 40–50% PEG 4,000 or 50% PEG 1500. The cells are then seeded in wells of culture plates and grown on a selective medium. The supernatants are tested for reactivity against purified βXIIa or other βXIIa antigen, for example, by a solid phase enzyme immunoassay, for example, using peroxidase-labelled anti-mouse IgG. All wells showing specificity for βXIIa are generally taken for further secondary screening. The secondary screening consists, for example, of screening all specific antibodies for binding in solution to βXIIa or to a βXIIa antigenic fragment that has been radiolabelled. These are preferably titrated to determine the antibody dilution required for 50% B max. Dose-response curves against cold, that is to say nonlabelled, βXIIa or the corresponding cold antigenic fragment, and also against Factor XII, plasmin and fibronectin are preferably generated. The extent of cross reaction may be determined according to the following formula I:

$$\frac{\text{Weight of Cold Standard βXIIa to Achieve 50\% } B \text{ max}}{\text{Weight of Cross-Reactant to achieve 50\% } B \text{ max}} \times 100$$

(If an antigenic fragment has been used instead of βXIIa, this should be substituted in the above formula.)

Those antibodies showing a pre-determined apparent cross reactivity to factor XII, preferably of 1.5% or less, and more preferably 1% or less are taken forward. Scatchard analysis may be done on the dose-response data to produce values for the affinity constants for each antibody. Those having affinity constants of at least $10^{10}M^{-1}$ are generally taken forward for cloning. Successful clones are generally isotyped. The cells are then preferably sub-cloned by limiting dilution and again screened, generally using an enzyme immunoassay, for the production of antibodies to βXIIa. A selected sub-clone from each cloning may also be evaluated with respect to specificity and dose response using a radioimmunoassay.

A further screening process, using αXIIa as antigen, may be incorporated at a suitable point if, for particular purpose, it is desired to select clones that produce a monoclonal antibody that is shown to bind to both αXIIa and βXIIa or to βXIIa only, or to confirm the binding characteristics of an antibody produced by a chosen clone. For such screening there may be used an αXIIa preparation obtained according to the method of Fujikawa & Davie (see above). If, however, αXIIa screening is carried out after βXIIa screening it is not generally necessary to subject an αXIIa-containing Factor XII preparation to the benzamidine-agarose chromatoraphy described. It is generally sufficient to establish that the preparation is free from βXIIa. As indicated above, it is generally preferable to use a liquid phase assay rather than a solid phase assay, for example, an assay that involves the displacement by αXIIa of radiolabelled βXIIa from the antibody.

Sub-cloned hybridoma cells may be injected intraperitoneally into BALB/C mice for the production of ascitic fluid. The immunoglobulin may be precipitated from ascites fluid, for example, at 4° C. using saturated ammonium sulphate solution (equal volume). The precipitate is preferably purified, for example, it may be centrifuged, dissolved, for example, in 50 mM Tris-HCl buffer pH 7.5 (volume equal to original ascites volume) and then dialyzed against the same buffer. The immunoglobulin fraction may then be further purified by anion exchange chromatography, for example, the protein solution may be applied to a Mono-Q anion exchange column (Pharmacia) and eluted using a salt gradient in the same buffer according to the manufacturer's recommendations. The fractions containing immunoglobulin are generally pooled and frozen at −20° C. for storage.

Alternatively, hybridoma cells may be grown in culture for antibody production and the antibody isolated essentially as described above for ascites fluid.

Although the hybridomas described herein are derived from mouse spleen cells, the invention is not limited to hybridomas of murine or part-murine origin. Both fusion partners (spleen cells and myelomas) may be obtained from any suitable animal.

The present invention may involve the use of a polyclonal antiserum that binds to βXIIa.

Methods used to produce polyclonal antibodies are well known see, for example, "Practice and Theory of Enzyme Immunoassays", P. Tijssen, Laboratory Techniques in Biochemistry and Molecular Biology, R. H. Burden and P. H. Van Knippenberg (Eds), Elsevier, 1985 and Introduction to Radioimmunoassay and Related Techniques, T. Chard, ibid, 3rd Edition, 1987. Polyclonal antisera may be produced, for example, in sheep or rabbit using Factor βXIIa, for example, conjugated to another protein, or Factor XII, as antigen.

As indicated above, the present invention also provides a method of detecting and/or determining Factor XIIa or βXIIa in a sample, which comprises subjecting the sample to a qualitative or quantitative immunoassay that comprises an interaction between an antigen and an antibody and the detection and/or determination of any resulting antibody-antigen complex, characterised in that the antibody is a monoclonal antibody of the present invention.

The present invention further provides a method of carrying out an immunoassay for an antigen in a sample of fluid, which assay involves an interaction between the antigen and an antibody that binds thereto and also involves determining the amount of antigen present in the sample, by reference to results obtained using predetermined amounts of a known antigen, characterised in that the antibody is a monoclonal antibody of the invention and the known antigen is Factor βXIIa.

Methods of carrying out immunoassays are well known cf for example, Methods in Enzymology, H. Van Vunakis and J. J. Langone (Eds), 1981, 72(B); Practice and Theory of Enzyme Immunoassays, P Tijssen, Laboratory Techniques in Biochemistry and Molecular Biology, R. J. Burden and P. H. Van Knippenberg (Eds), Elsevier, 1985; Introduction to Radioimmunoassay and Related Techniques, T. Chard, ibid, 3rd Edition, 1987; and Methods in Enzymology, H. Van Vunakis and J. J. Langone (Eds) 1981, 74(C).

As indicated above, immunoassay techniques, both qualitative and quantitative, are well known and include ELISA (enzyme linked immunosorbent assays), Western blotting, fluid phase precipitation assays, coated particle assays, competitive assays, sandwich assays, including forward, reverse and simultaneous sandwich assays, and solid phase radio immunoassays (SPRIA).

Of these, ELISA and SPRIA may be particularly convenient in the present case. Accordingly, samples of a monoclonal antibody according to the present invention may be adsorbed on to a solid phase support, for example, a plastics or other polymeric material, for example the wells of plastics microtitre plates, samples of plasma under investigation or a standard solution are incubated in contact with the antibody reagent and any resulting bound Factor XIIa or βXIIa detected using a labelled antibody that is capable of binding to the bound Factor or to the standard, for example, to a different epitope on the molecule. The labelled antibody may be polyclonal or monoclonal. Any appropriate radioisotope may be used as the label, for example a β-emitter or a α-emitter, examples being $^{125}$I, $^{131}$I, $^{3}$H, and $^{14}$C. An enzyme label is, for example, alkaline phosphatase, using phenolphthalein monophosphate as substrate. An enzyme reaction may be followed using an electrochemical method. As an alternative to the use of a labelled antiantibody, bound XIIa or βXIIa may be determined directly by using a chromogenic substrate.

Instead of adsorbing a monoclonal antibody of the invention on a solid support, βXIIa itself or an antigenic fragment thereof, may be bound for use in a competitive assay. A further alternative is to use labelled, for example, radiolabelled βXIIa or an antigenic fragment thereof in a competitive assay.

An example of a radioimmunoassay for use according to the invention is as follows: A dose-response curve using a monoclonal antibody $^{125}$I-labelled βXIIa, βXIIa standard solutions and anti-mouse IgG coupled to a solid support, for example, SEPHACRYL S-1000 may be demonstrated according to the following method: Monoclonal antibody ascitic fluid is diluted with Assay Buffer, for example, a buffer comprising 50 mM Tris-HCl pH 7.4 containing 0.15 m NaCl, 0.25% BSA, 10 mM EDTA, 3 mM NaN and 0.1% Triton. In duplicate assay tubes is added an sample of each of a monoclonal antibody solution, a $^{125}$I-radiolabelled βXIIa solution and purified βXIIa standard solution in Assay Buffer. The standard solutions are prepared from a βXIIa stock solution. Control tubes to give total counts were prepared using Assay Buffer and tracer solution. All tubes are mixed and then incubated. After this a sample of a suspension containing an optimal amount of anti-mouse IgG coupled to a solid support was added to each tube (except totals) and the tubes are then incubated with shaking. After this step preferably sucrose buffer (Assay Buffer+10% w/w sucrose) is layered underneath the reaction mixture in each tube (except totals), for example, using a peristaltic pump. The solid support-coupled anti-mouse IgG is allowed to sediment after which the liquid is removed from each tube. All tubes including totals are then counted. The % bound may be calculated by dividing the counts achieved for each βXIIa standard by the total counts. The total counts added are, for example, 10,000 cpm. In the above radioimmunoassay an antigenic fragment of βXIIa may be substituted for βXIIa.

The present invention further provides a kit for carrying out an immunoassay of the present invention, which kit comprises, each in a separate container or otherwise compartmentalized:
a monoclonal antibody of the invention and Factor βXIIa or an antigenic fragment thereof. The kit may comprise further components for carrying out an immunoassay, for example, as described above. The monoclonal antibody of the invention may be unlabelled or labelled. It may be immobilized on a solid support.

A kit according to the invention may comprise, for example,
a)(i) a monoclonal antibody of the present invention, or
(ii) Factor βXIIa or an antigenic fragment thereof, or
(iii) an antibody directed against an antibody of the invention;
b)(i) labelled antibody capable of reacting directly or indirectly with Factor βXIIa, or (ii) labelled Factor βXIIa, or (iii) a chromogenic substrate for Factor βXIIa; and c) a control reagent, which is purified Factor βXIIa or an antigenic fragment thereof.

A component a)(i), a)(ii) or a)(iii) may be bound to a solid support, if desired.

A kit may also comprise further components, each in a separate container, for example, wash reagent solution and substrate solution.

Polyclonal antisera or, especially, a monoclonal antibody of the invention, may be used in affinity chromatography as an immunosorbent in the purification of Factor βXIIa or an antigenic fragment thereof and the present invention provides an immunosorbent comprising a monoclonal antibody of the present invention, generally absorbed on or otherwise carried by a solid support in a conventional manner (see below), and relates to a method of purifying Factor βXIIa or an antigenic fragment thereof using such a supported antibody (immunosorbent). The purified Factor βXIIa or antigenic fragment may be used. as the control reagent in the method of the present invention for determining Factor βXIIa. Conversely, the invention also relates to an immunosorbent comprising Factor βXIIa or an antigenic fragment thereof, generally absorbed on or otherwise carried by a solid support in a conventional manner (see below).

The present invention also provides a method of screening and/or a method of purifying anti-Factor βXIIa antibodies and antisera using such a supported antigen (immunosorbent). It is advantageous to screen monoclonal antibodies for specificity and/or affinity for βXIIa using an antigenic fragment of βXIIa preferably in the form of an immunosorbent as described above. If desired, further screening and/or purification may be carried out using Factor αXIIa or an antigenic fragment thereof immobilized on a solid support as an immunosorbent.

Polyclonal antibodies may be purified, especially to increase the content of anti-Factor βXIIa antibodies, for example, by contacting the polyclonal antibodies with Factor βXIIa or an antigenic fragment thereof. The polyclonal antibodies preferably are contacted with an antigenic fragment of βXIIa immobilised on a solid support, and the resulting bound antibodies are released. The specificity and affinity properties of a crude polyclonal antibody preparation can be improved substantially by such a method, so the resulting polyclonal antibodies are made more suitable for use in a commercial assay.

A monoclonal mouse antibody that binds to βXIIa may be covalently coupled to CNBr-activated SEPHAROSE-4B (Pharmacia) according to the manufacturer's instructions. Such a column may be used to isolate a βXIIa antigen, for example, to isolate βXIIa from plasma or βXIIa or an antigenic fragment thereof from a digest of Factor XII, as appropriate. Bound βXIIa antigen may be eluted from the column using, for example, 4M guanidine, and the antigen detected in the effluent, for example, βXIIa may be detected in the effluent fractions by enzymatic activity using S-2302 peptide substrate (Kabi) or using $^{125}$I labelled βXIIa.

A βXIIa antigen as described above that is to say, βXIIa itself or an antigenic fragment thereof, may, for example, be coupled to thiol-activated SEPHAROSE (Pharmacia) via one or more thiol groups on intrinsic or introduced cysteine moieties according to the manufacturer's instructions. Factor αXIIa or an antigenic fragment thereof may be coupled analogously.

As indicated above, there appears to be an enzyme/substrate relationship between Factor XIIa, for example Factor βXIIa, activity and Factor VII activity, which suggests that Factor XIIa, for example Factor βXIIa, activity can be used instead of Factor VII activity as an indicator of the risk of heart disease, particularly ischaemic heart disease (IHD) and acute myocardial infarction (AMI).

Results of investigations into turnover of $^{125}$I-labelled Factor XII in rabbits fed on normal or cholesterol-supplemented diets indicate that, although there is little change in the half-life and pool size of Factor XII in the extravascular and intravascular compartments, and although there is little change in the fractional catabolic rate, the absolute catabolic rate in the rabbits fed on a cholesterol-supplemented diet is greater than that in rabbits fed on the standard diet. Rabbits have much lower kallikrein levels that man, so it would be expected that an increase in catabolic rate of Factor XII would be even more marked in man in corresponding circumstances. The significance of the increased catabolic rate of Factor XII is the effect this will have on Factor VII activity. These results indicate that Factor XIIa, for example Factor βXIIa, may be suitable as an indicator of the risk of AMI.

Accordingly, it is proposed that data resulting from an immunoassay of the invention carried out on a sample of plasma obtained from a subject will be useful in indicating the risk to that subject of heart disease, in particular Ischaemic Heart Disease and/or Acute Myocardial Infarction. A correlation between the results obtained for an individual and the risk of heart disease, for example, ischaemic heart disease and especially acute myocardial infarction for that individual may be made by studying these parameters in a number of individuals, preferably including individuals considered on the basis of other criteria to be at risk and individuals not considered to be at risk. The larger the population investigated the better will be the accuracy of the correlation. The design and conduct of such epidemiological studies is known, see, for example, the Northwick Park Hospital and Framingham Studies referred to above. Assessment of the risk to an individual of heart disease, for example AMI, may be made by comparison of the data determined for that individual with that determined in epidemiological studies, for example as described above.

The method and other embodiments of the present invention are also useful in investigations of the mechanisms involved in blood coagulation and in the study of thrombotic disorders.

The following Examples 2, 3, 5 to 7, and 9 illustrate the invention, but are not intended to limit the invention in any way.

EXAMPLE 1

Isolation and purification of Factors XII and βXIIa

Isolation of Factor XII from fresh or frozen human plasma was carried out using a combination of ammonium sulphate precipitation and anion exchange chromatography essentially as described by K. Fujikawa and E. W. Davies, Methods Enzymol, 1981, 80, 198). From 6.5 liters of plasma the yield of factor XII was 53 mg.

The preparation of Factor βXIIa from Factor XII by tryptic digestion was carried out using the method previously described by B. A. McMullen and K. Fujikawa JBC, 1985 260, 5328; and by K. Fujikawa and B. A. McMullen JBC, 1983, 258, 10924). (JBC is Journal of Biological Chemistry.)

The 53 mg of Factor XII were dialyzed against 8 liters of 50 mM Tris/75 mM NaCl, pH 8.0 at 4° C. overnight. The protein solution was warmed to 37° C., 0.7 mg trypsin was added and equilibrated at 37° C. for 15 minutes. 1.4 mg of soya bean trypsin inhibitor (SBTI) was then added to stop the digestion and the solution was kept at 37° C. for a further 15 minutes. The βXIIa was separated immediately from the other components using DEAE-SEPHACEL. The column was washed with Tris/75 mM NaCl pH 8.0 until some protein had washed off and then a gradient was started using 50 mM Tris/75 mM NaCl→50 mM Tris/500 mM NaCl pH 8.0. Two protein peaks were eluted during the gradient. βXIIa has no clotting activity, unlike Factor XII. The activity of the product in the eluate was measured using the synthetic substrate S-2302 (Kabivitrum) and the rate of change of absorbance at 405 nm. βXIIa appears in the second peak. 14 mg of βXIIa were obtained (70% from Factor XII).

FIG. 1 of the accompanying drawings is a plot of absorbance at 280 nm against time for the eluate of the DEAE-SEPHACEL column and shows βXIIa in the second peak.

Figure 2A:
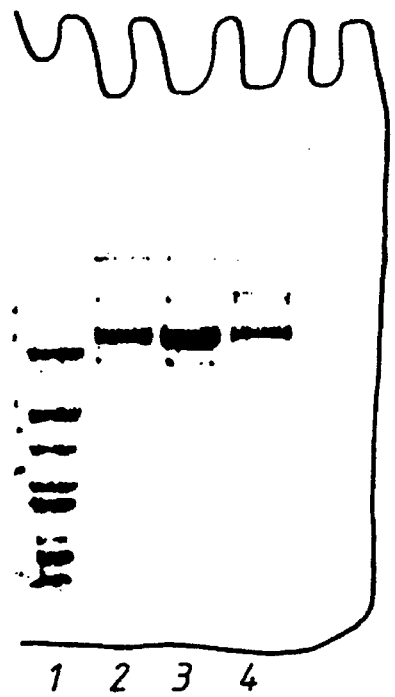
FIGS. 2a and 2b—SDS-PAGE gels for Factors XII and βXIIa, respectively. $E_{280}^1$ =1.42 in FIG. 2a and $E_{280}^1$ =1.52 in FIG. 2b. Track 1 of both gels consists of bands formed by molecular weight standards as follows: 20,100; 24,000; 29,000; 36,000; 45,000; and 66,000. Tracks 1, 2 and 3 of FIG. 2a show the bands obtained for three fractions from the Factor XII peak on "S-SEPHAROSE" chromatography (which was used instead of CM-cellulose chromatography described by Fujikawa). Tracks 2 to 7 of FIG. 2b show the bands obtained for fractions 32 to 27 respectively of the eluate of the DEAE-"SEPHACEL" chromatography.
Figure 2B:
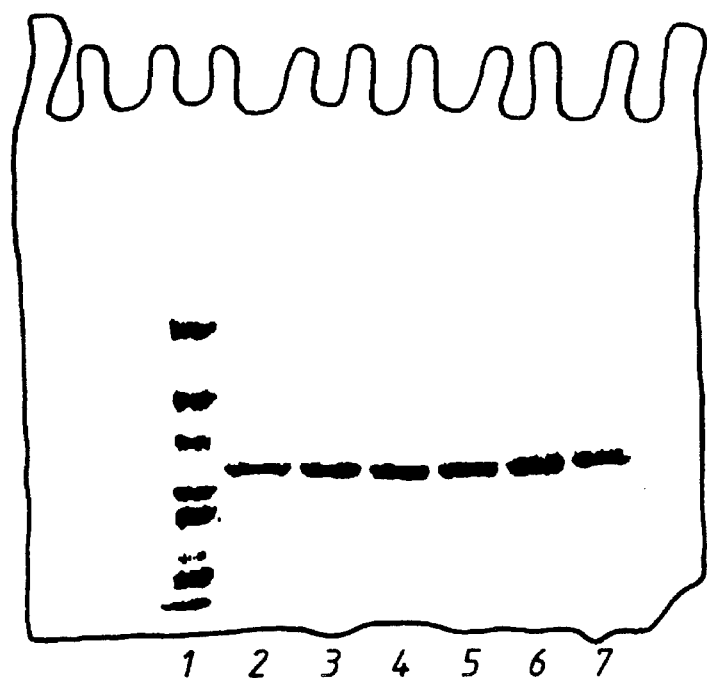

Purity was confirmed by SDS-PAGE under reducing and non-reducing conditions according to the method of Laemmli. (V. K. Laemmli, Nature, 1970, 227, 680). The acrylamide concentration was 3% in the spacer gel and 10% in the separating gel. Protein bands were detected by Coomassie blue staining. FIGS. 2a and 2b of the accompanying drawings show of SDS-PAGE gels for XII and βXIIa, respectively. $E_{280}^1$ =1.42 in FIG. 2a and $E_{280}^1$ =1.52 in FIG. 2b. Track 1 of both gels consists of bands formed by molecular weight standards as follows: 20,100; 24,000; 29,000; 36,000; 45,000; and 66,000. Tracks 1, 2 and 3 of FIG. 2a show the bands obtained for three fractions from the Factor XII peak on S-SEPHAROSE chromatography (which was used instead of the CM-cellulose chromatography described by Fujikawa). Tracks 2 to 7 of FIG. 2b show the bands obtained for fractions 32 to 27 respectively of the eluate of the DEAE-SEPHACEL chromatography.

EXAMPLE 2

(a) Production of murine specific monoclonal antibodies

Murine monoclonal antibodies to human βXIIa were prepared by a modification of the method of Kohler and Milstein (G. Kohler and C. Milstein, Nature, 1975, 256, 495).

Female BALB/C mice were immunized by intraperitoneal injection of 20 μg of βXIIa conjugated to a) bovine thyroglobulin or b) a purified protein derivative of tuberculin. The conjugation was done by either a carbodimide method or using a heterobifunctional reagent. The immunogen was presented in complete Freunds adjuvant. At 3 week intervals the mice were boosted with 20 μg of conjugated βXIIa in complete Freunds adjuvant. A prefusion boost was given intravenously 3 days prior to sacrifice.

The antibody response was monitored by RIA antisera curve analysis using $^{125}$I- radiolabelled βXIIa prepared by the chloramine-T method (P. J. McConahey and F. J. Dixon, Int. Arch. Allergy Appl. Immunol, 1966, 29, 185). Purity was confirmed using autoradiography of SDS-PAGE gels run under reducing conditions. Immune mouse spleen cells were fused with NSO mouse myeloma cells in the presence of 40–50% PEG 4,000. The cells were then seeded in wells of culture plates and grown on selective medium. The supernatants were tested for reactivity against purified βXIIa by a solid phase enzyme immunoassay using peroxidase-labelled anti-mouse IgG. Briefly, the wells of a 96 well microtitre plate were coated with purified βXIIa (100 μl of a 10 μg/ml solution in phosphate buffered saline, PBS) and then blocked using 2% BSA (bovine serum albumin) in PBS. The cell culture supernatants were added to the wells and after incubation for 1 hour at 37° C. the wells were washed 3 times and peroxidase-labelled anti-mouse IgG was added at an optimal dilution. After a further incubation at 37° C. for 1 hour the wells were again washed and 100 μl of substrate solution was added (6 mM $H_2O_2$ and 40 mM O-phenylenediamine in 0.1M citrate pH 5.0). The color development was stopped with 100 μl of 3M HCl and the absorbance was measured at 492 nm.

All wells showing specificity for βXIIa were taken for further secondary screening. The secondary screening consisted of screening all specific antibodies for binding to radiolabelled βXIIa in solution. These were titrated to determine the antibody dilution required for 50% B max. Dose response curves against cold (non-labelled) βXIIa, factor XII, plasmin and fibronectin were generated. The extent of cross reaction was determined on the following formula:

$$\frac{\text{Weight of Cold Standard }\beta\text{XIIa to Achieve 50\% }Bmax}{\text{Weight of Cross-reactant to achieve 50\% }Bmax} \times 100$$

Those antibodies showing an apparent cross reactivity to Factor XII of less than 1.5% were taken forward. Scatchard analysis was done on the dose-response data to produce values for the affinity constants for each antibody. Those having affinity constants of at least $10^7 M^{-1}$, and preferably up to $10^{10} M^{-1}$ were taken forward for cloning. Successful clones were isotyped.

The cells were then sub-cloned by limiting dilution and again screened using enzyme immunoassay for the production of antibodies to βXIIa. A selected clone from each cloning was also evaluated using radioimmunoassay with respect to specificity and dose response. Sub-cloned hybridoma cells secreting antibody to βXIIa were injected intraperitoneally into BALB/C mice for the production of ascitic fluid. Six cloned hybridomas that produce ascites fluid containing monoclonal antibodies to βXIIa were obtained.

b) Isolation of Immunoglobulin Fraction from Ascites Fluid

The immunoglobulin fraction was precipitated from ascites fluid at 4° C. using saturated ammonium sulphate solution (equal volume). The precipitate was centrifuged, dissolved in 50 mM Tris-HCl buffer pH 7.5 (volume equal to original ascites volume) and then dialyzed against the same buffer. The protein solution was then applied to a Mono-Q anion exchange column (Pharmacia) and eluted using a salt gradient in the same buffer according to the manufacturer's recommendations. The fractions containing immunoglobulin were pooled and frozen at –210° C. for storage. The yield was generally from 1 to 5 mg purified antibody/ml of ascitic fluid.

c) Enzyme Labelling of Antibodies

Purified immunoglobulin from ascitic fluid or polyclonal antisera was conjugated to alkaline phosphatase using the thiol-maleimide method (E. Ishikawa et al., J. Immunoassay, 1983 4, 209). The conjugates obtained were purified by gel-filtration chromatography using SEPHACRYL S-300 (Pharmacia).

EXAMPLE 3

Preparation of Affinity Support

Monoclonal mouse antibody to βXIIa was covalently coupled to CNBr activated SEPHAROSE-4B (Pharmacia) according to the manufacturer's instructions. From 5 to 10 mg of purified IgG was bound to 1 g of unswollen gel. This column was used to isolate βXIIa from plasma of from tryptic digests of Factor XII. 4M guanidine was used to elute bound βXIIa from the column and βXIIa was detected in the effluent fractions by enzymatic activity using S-2302 peptide substrate (Kabi) or by using $^{125}$I-labelled βXIIa.

EXAMPLE 4

Polyclonal Antisera

Polyclonal antisera to Factor XII and βXIIa were raised in sheep or rabbits by standard methods using native Factor XII and conjugated βXIIa, see Methods in Enzymology, H. Van Vunatis and J. J. Langone (Eds) 1981, 72 (B) and 1983 92 (E).

EXAMPLE 5

Radioimmunoassay for βXIIa

A dose-response curve using monoclonal antibody 202/2.6 obtained according to the method described in Example 2. $^{125}$I-labelled βXIIa, βXIIa standard solutions and sheep anti-mouse IgG coupled to SEPHACRYL S-1000 (SAM-SEPHACRYL) was demonstrated accordingly to the following method: Monoclonal antibody 202/2.6 ascitic fluid was diluted 1:1000 with Assay Buffer (50 mM Tris-HCl pH 7.4 containing 0.15M NaCl, 0.25% BSA, 10 mM EDTA 3 mM NaN3 and 0.1% Triton). In duplicate 4 ml volume polystyrene assay tubes was added: 50 μl of monoclonal antibody solution, 50 μl of radiolabelled βXIIa solution and 100 μl of pure βXIIa standard solution in Assay Buffer. The standard solutions were prepared by doubling dilutions of a βXIIa stock solution. The concentration of the stock solution was calculated using the following formula:

$E^1_{280} = 15.2$ (K. Fujikawa and B. A. McMullen JBC, 280 1983, 258, 10924).

Figure 3:
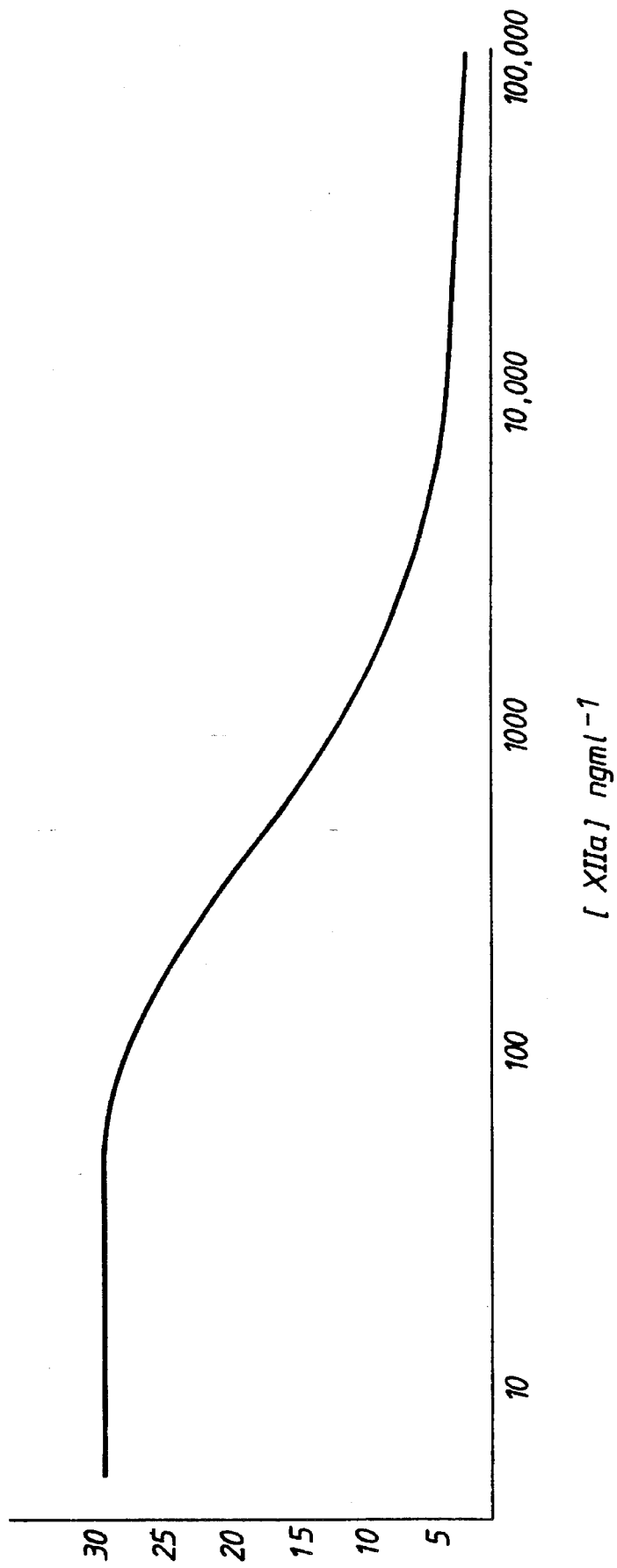
FIG. 3—A dose-response curve of Factor βXIIa concentration against % bound $^{125}$I βXIIa. The % bound was calculated by dividing the counts achieved for each Factor βXIIa standard by the total counts. The total counts added were 10,000 cpm.

Control tubes to give total counts contained 150 μl of Assay Buffer and 50 μl of tracer solution. All tubes were Vortex mixed and then incubated at 21°±1° C. for 19 hours. After this period 50 μl of a suspension containing an optimal amount of SAM-SEPHACRYL was added to each tube (except totals) and the tubes were then incubated at 21°±1° C. for 1 hour with shaking. After this step 1.5 ml of sucrose buffer (Assay Buffer+10% w/w sucrose) was layered underneath the reaction mixture in each tube (except totals) using a peristaltic pump. The SAM-SEPHACRYL was allowed to sediment at 21°±1° C. for 30 minutes after which the liquid was removed from each tube, leaving approximately 0.3 ml. All tubes including totals were then counted for 60 seconds in a Multiwell gamma counter. The results are presented in Table 1 and FIG. 3 of the accompanying drawings, which is a dose-response curve of βXIIa concentration against % bound $^{125}$I βXIIa. The % bound was calculated by dividing the counts achieved for each βXIIa standard by the total counts. The total counts added were 10,000 cpm.

TABLE 1

| Concentratin of Cold βXIIa added (μg/ml) Bound | % Bound | | |
|---|---|---|---|
| | 1 | 2 | Mean % |
| 90 | 2.1 | 1.8 | 2.0 |
| 45 | 2.3 | 2.4 | 2.4 |
| 22.5 | 2.6 | 3.0 | 2.8 |
| 11.3 | 3.4 | 3.2 | 3.3 |
| 5.6 | 4.6 | 4.0 | 4.3 |
| 2.81 | 5.8 | 6.2 | 6.0 |
| 1.41 | 9.3 | 9.6 | 9.4 |
| 0.73 | 13.6 | 12.8 | 13.2 |
| 0.35 | 19.0 | 19.5 | 19.2 |
| 0.18 | 24.0 | 25.0 | 24.5 |
| 0.09 | 26.7 | 26.7 | 26.7 |
| 0.05 | 29.8 | 27.9 | 28.8 |
| 0.02 | 27.7 | 28.4 | 28.0 |
| 0.01 | 29.2 | 29.4 | 29.3 |
| 0.005 | 28.7 | 28.9 | 28.8 |
| 0.00 | 29.0 | 30.2 | 29.6 |

EXAMPLE 6

Production of βXIIa monoclonal antibodies

Murine monoclonal antibodies to human βXIIa were prepared by the general method of Kohler and Milstein (G. Kohler & C. Milstein, Nature, 1975, 256, 495):

(i) Preparation of the immunogen

The immunogen was prepared by conjugating βXIIa to a purified protein derivative of tuberculin (PPD) using the heterobifunctional reagent sulpho SMCC (P. J. Lachmann et al., Synthetic Peptides as Antigens, Ciba Foundation Symposium 119, 25–57, 1986):

N-Succinidimyl 3-(2-pyridyldithio)propionate (SPDP, 6 mg) was dissolved in ethanol (5 ml). A 5 mg/ml solution of PPD (for Heaf Test, Statens Serum Institut, Denmark) in 0.1M PBS pH 7.4 was prepared. A mixture of PPD solution (1 ml) and SPDP solution (5 μl) was incubated for 30 minutes at room temperature, after which the preparation was dialysed against 0.1M PBS pH 7.4. Free thiol groups were exposed by incubating the derivatised PPD with dithiothreitol (at a 50 mM concentration) for 30 minutes at room temperature. The reaction mixture was then dialyzed against 0.1M sodium acetate buffer pH 4.5 containing 100 mM sodium chloride.

Purified βXIIa, prepared as described in Example 1 above, was dialyzed against 0.1M borate buffer pH 8.0, and the final concentration was adjusted to 5 mg/ml. A solution of sulpho-succinimidyl 4-(N-maleiimidomethyl) cyclohexane-1-carboxylate (sulpho-SMCC) was prepared in 0.1M borate buffer pH 8.0. 100 μl of this solution was added to the βXIIa solution such that the molar ratio sulpho-SMCC:βXIIa was 100:1. The mixture was incubated at room temperature for 30 minutes and then dialyzed against 0.1M PBS pH 7.4.

Equal weights of activated βXIIa and activated PPD were incubated for 18 hours at 4° C. and the mixture was then dialyzed against 0.1M PBS pH 7.4. This material was used for immunization.

(ii) Production of spleen lymphocytes

Female C57/B10 or BALB/C mice were primed with BCG, and one day later were immunised with 20 μg of the βXIIa-PPD immunogen in complete Freund's adjuvant. At two week intervals, the mice were boosted with 20 μg of the immunogen in incomplete Freund's adjuvant. Two weeks after the second boost, a pre-fusion boost was given intravenously, and three days later the animals were sacrificed.

The immune response of the mice was monitored by RIA using $^{125}$I-radiolabelled βXIIa prepared using the chloramine-T method with an uptake of approximately 50–75 μCi/mg. Purity was confirmed using autoradiography of SDS-PAGE gels run under reducing conditions.

The RIA procedure was as follows: To 100 μl of diluted labelled βXIIa (15,000 cpm/tube) was added 100 μl of antiserum diluted in assay buffer II (phosphate buffered saline containing 0.5% (w/v) Tween (Trade Mark), 1% (w/v) bovine serum albumin (BSA) and 0.01% (w/v) sodium azide). A further 100 ul of buffer was added and the mixture was incubated at 20° C. for 20 hours. The bound labelled βXIIa was separated using a second antibody system (Dako anti-mouse antibody at 1/100 in assay buffer II containing 6% (w/v) PEG and 50 μg of 1/100 normal mouse serum). After decanting off, the supernatant was read in a gamma counter, 60 s/tube.

(iii) Fusion Protocol

Spleen cells were removed from responding mice having an antibody titre greater than 1/5,000 and preferably greater than 1/20,000, gently homogenized, washed three times and then resuspended in Dulbecco's modified Eagle's medium (DMEM). The myeloma cell line used was NSO (uncloned) obtained from the MRC Laboratory of Molecular Biology, Cambridge. The myeloma cells, in log growth phase, were washed in DMEM.

Spleen cells (1×10$^8$) were mixed with myeloma cells (7×10$^7$), centrifuged, and the liquid removed. The resultant cell pellet was placed in a vessel in a 37° C. water bath. Over a period of one minute, 1 ml of a 50% (w/v) solution of polyethylene glycol (PEG) 1500 in saline Hepes pH 7.5 was added and the mixture stirred gently for one and a half minutes. Over a period of five minutes 50 ml of serum-free DMEM was added, then the mixture was centrifuged. The supernatant was discarded and the cell pellet resuspended on 10 ml of DMEM containing 18% foetal calf serum (FCS). A 10 µl aliquot of the resulting cell suspension was added to each of the 480 wells of standard multiwell tissue culture plates. Each well contained 2 ml of standard HAT medium (hypoxanthine, aminopterin, thymidine) and a feeder layer of BALB/C cells at a concentration of $5 \times 10^4$ macrophages/well. The wells were maintained at 37° C. in 9% $CO_2$ air at approximately 90% humidity. The wells were analyzed for monoclonal antibody production as described below. From those wells that yielded antibody-producing cells, cells were removed and cloned by the standard limiting dilution cloning procedure.

(iv) Screening of hybridomas using solid phase enzyme immunoassay

All wells showing hybrids were screened using a solid phase enzyme immunoassay (EIA) as follows:

The wells of a 96 well microtitre plate (Nunc Immunoplate, Polysorb Catalogue No. 4-75094) were coated overnight with purified βXIIa obtained as described in Example 1 above, using 100 µl aliguots of a 1 µg/ml solution in MES-saline (20 mM 2-(N-morpholinoethane sulphonic acid), 150 mM sodium chloride, pH6.5) and then blocked using 1% milk protein in MES-saline. The cell culture supernatants diluted 1:1 in augmented MES-saline (MES-saline containing 0.05% (w/v) Tween, 1% (w/v) BSA and 0.05% (w/v) Thiomersal) were added to the wells and after incubation for 1 hour at 37° C. the wells were washed three time with PBS containing 0.05% (w/v) Tween and 0.05% (w/v) Thiomersal, and horse radish peroxidase-labelled anti-mouse IgG (Biorad, anti-heavy chain specific, 1:2500 in augmented MES-saline was added. After a further incubation at 37° C. for 1 hour the wells were again washed and 100 µl of substrate solution added (6 mM$H_2O_2$ and 40 mMo-phenylenediamine in 0.1M citrate, pH 5.0). The color development was stopped with 100 µl of 3M HCl, and the absorbance was measured at 492 nm. Wells showing a good discrimination between the binding of βXIIa and Factor XII were titrated in an antisera curve analysis versus $^{125}I$-labelled βXIIa. All wells showing binding of the labelled βXIIa and titres greater than 1 in 10 were presented for analysis of the dose response and of the extent of cross reaction with Factor XII using formula I:

$$\frac{\text{Weight of Cold Standard βXIIa to Achieve 50\% } Bmax}{\text{Weight of Cross-Reactant to Achieve 50\% } Bmax} \times 100$$

From this preliminary data 6 hybridomas having an apparent cross reactivity of 1.5% were selected for cloning.

A representative clone from each line was further analyzed by RIA for cross-reaction with Factor XII (FXII), plasmin and fibronectin. Table 2 gives the dose response curves for three preferred clones to determine the apparent cross reactivity to Factor XII.

TABLE 2

RIA Dose Response To Determine Apparent Cross Reactivity Of Certain Clones to Factor XII

| | Clone Number | | |
|---|---|---|---|
| | 201/9 | 2/215 | 2/15 |
| | | % Bound | |
| Concentration of βXIIa ng/ml | | | |
| 0.0 | 100 | 100 | 100 |
| 0.5 | 95 | 87 | 87 |
| 1.0 | 91 | 87 | 79 |
| 2.5 | 76 | 56 | 57 |
| 5.0 | 58 | 33 | 40 |
| 10.0 | 32 | 17 | 21 |
| 50.0 | 6 | 3 | 4 |
| 100.0 | 4 | 2 | 2 |
| Concentration of XII ng/ml | | | |
| 50 | 97 | 98 | 83 |
| 100 | 94 | 87 | 73 |
| 500 | 71 | 37 | 26 |
| 1000 | 51 | 19 | 13 |
| 2000 | 30 | 9 | 7 |

Scatchard analysis was performed on the dose response curves to give affinity constant (Ka) values. The data for three preferred cell lines is given in Table 3 below, together with some data relating to a further clone having a high degree of cross-reactivity to Factor XII:

TABLE 3

RIA Dose Response and Apparent Cross-Reactivity Study of Certain anti-βXIIa antibodies

| Clone Number | Titre | Bo/T % | βXIIa ng/ml | | | | Ka (M$^{-1}$) |
|---|---|---|---|---|---|---|---|
| 201/9 | 200,000 | 30 | 6.5 | 0.7 | <0.1 | <0.1 | $3.5 \times 10^{10}$ |
| 2/15 | 20,000 | 25 | 3.2 | 1.4 | <0.1 | <0.1 | $6.5 \times 10^{10}$ |
| 2/215 | 20,000 | 12 | 3.1 | 1 | <0.1 | <0.1 | $1 \times 10^{10}$ |
| 202/16.1.9 | 5,000 | — | 2,000 | 67 | — | — | $5.46 \times 10^{10}$ |

(v) Assessment of Corrected Cross-Reactivity with Factor XII

A factor to be taken into consideration in assessing the cross-reactivity of an anti-βXIIa antibody with Factor XII is that even "pure" Factor XII is almost inevitably contaminated with small amounts of XIIa (Silverberg and Kaplan, Blood 60, 1982, 64–70). Although this contamination is not significant for most purposes, the presence of even small amounts of XIIa will clearly affect the results of studies of cross-reactivity of anti-βXIIa antibodies with Factor XII. Accordingly, it was considered necessary to obtain an estimate of the level of βXIIa in the samples of Factor XII used for the cross-reactivity determinations. The chromogenic assay for XIIa, which can detect contamination at levels >10 ng/ml was used.

Measurement of XIIa concentration in Factor XII sample

The amidolytic activity of XIIa present in the "pure" factor XII was determined by the addition of 200 μl of 2 mM Pro-Phe-Arg-p-nitroanilide (β2302, Kabi) in 65 mM Tris, 135 mM sodium chloride, 0.01% BSA, pH 8 to 50 μl of βXIIa standards or of the Factor XII samples, which have predetermined concentrations of XII (determined by measurement of the extinction co-efficient, see Fujikawa & McMullen, loc. cit.). The hydrolysis of the substrate was measured by determination of the absorbance at 405 nm after incubation at room temperature for 60 minutes. The amidolytic activity of the samples was compared with that of the βXIIa standards. The results obtained are presented in Table 4 below.

TABLE 4

| Amidolytic activity of Factors βXIIa and XII | | |
|---|---|---|
| Sample or Standard Concentration | Absorbance at 405 nm | βXIIa (ng/ml) |
| βXIIA STANDARDS | | |
| 0 | 0.06 | |
| 10 | 0.10 | |
| 25 | 0.15 | |
| 50 | 0.25 | |
| 100 | 0.41 | |
| FACTOR XII SAMPLS | | |
| 1200 | 0.09 | <10 |
| 12000 | 0.30 | 60 |
| 24000 | 0.50 | >100 |

The percentage contamination of Factor XII with βXIIa was calculated according to the following formula:

$$\frac{\text{Concentration of βXIIa in FACTOR XII}}{\text{Concentration of FACTOR XII}} \times 100$$

The results obtained indicate that the contamination of Factor XII by XIIa is within the range of from 0.5 to 0.8%.

Assessment of cross-reactivity of Factor XII with monoclonal antibody 2/215

An immunoassay for βXIIa was carried out using monoclonal antibody conjugates 201/9 and 202/16.1.9 as described in Example 7 below. The βXIIa standards and Factor XII sample concentrations used were as set out for the chromogenic test above. The results are shown in Table 5.

TABLE 5

| Cross Reactivity of 2/215 Using Monoclonal Antibody Conjugates | |
|---|---|
| Concentration of βXIIa ng/ml | Absorbance at 550 nm |
| 0.0 | 0.114 |
| 1.0 | 0.213 |
| 2.5 | 0.354 |
| 5.0 | 0.587 |
| 10.0 | 0.999 |
| 15.0 | 1.405 |
| 25.0 | 1.960 |
| Concentration of Factor XII μg/ml | Absorbance at 550 nm |
| 0.23 | 0.266 |
| 0.46 | 0.322 |
| 1.20 | 0.652 |
| 2.30 | 1.065 |
| 5.80 | 1.905 |

The apparent cross-reactivity was calculated to be in the region of 0.5%, but when contamination of the Factor XII with XIIa was taken into account as described above, the corrected cross-reactivity was found to be less than 0.1%.

(vi) Production of antibody

Sub-cloned hybridoma cells that secrete antibody to βXIIa were injected intra-peritoneally into BALB/C mice for the production of ascitic fluid or were grown in culture.

The immunoglobulin fraction was precipitated from ascites fluid at 4° C. using an equal volume of saturated ammonium sulphate solution. The precipitate was centrifuged, dissolved in a volume of 20 mM Tris-HCl buffer pH 7.5 (Buffer A) equal to the original volume of the ascites fluid, and then dialyzed against the same buffer. The protein solution was then fractionated on a Mono-Q (Trade Mark) anion exchange column (HR 10/10, Pharmacia) by means of FPLC (Trade Mark) equipment from Pharmacia. Elution was conducted using a gradient made with buffer A and buffer B (buffer A supplemented with 1M NaCl) at a flow rate of 2 ml per minute. The eluate was monitored at 280 nm and 1 ml fractions were collected. The fractions containing immunoglobulin were pooled and frozen at −20° C. for storage.

Essentially the same method was used to isolate the immunoglobulin fraction from culture fluid.

(vii) Deposit of hybridomas

Hybridoma cell lines have been deposited at the European Collection of Animal Cell Cultures, Division of Biologics, PHLS Centre for Applied Microbiology and Research, Porton Down, Salisbury SP4 0JG, England, as follows:

2/215 (BFx11a) deposited on 16 Jan. 1990, deposit number 90011606;

201/9 (ESBT4 1.1) deposited on 18 Jan. 1990, deposit number 90011893;

202/16.1.9 (ESBT 92.9) deposited on 25 Jan. 1990, deposit number 90012512.

EXAMPLE 7

Assay using monoclonal antibody 2/215

The wells of 96 well microtitre plates were coated overnight at 20°–25° C. with antibody 2/215 using 100 μl per well of a 5 μg/ml preparation of the antibody in a coating buffer (0.1M phosphate buffer, 0.15M sodium chloride containing 0.1% sodium azide, 0.02% gentamycin sulphate, pH 7.4.

Aliquots of 100 μl of a sample of human plasma or of βXIIa standards were added to the wells, and the plates were incubated at 20°–25° C. for 1 hour. Each well was then washed with wash buffer (10 mM borate buffer, 50 mM sodium chloride, 0.1% Triton-X-100, 0.05% sodium azide, pH 7.4) prior to the addition of a mixture of anti-βXIIa monoclonal antibodies 201/9 and 202/16.1.9 (202/16.1.9 being a high Factor XII cross reacting antibody) which antibodies had previously been conjugated to alkaline phosphatase using the thiol-maleiimide method (E. Ishikawa et al., J. Immunoassay, 1983, 4, 209). The antibody conjugates were each titrated against βXIIa to determine the optimal dilution. The conjugates were then mixed at these dilutions. The conjugate diluent is 0.1M sodium chloride, 1 mM magnesium chloride hexahydrate, 0.1M Tris, 0.1 mM zinc chloride, 0.1% (w/v) sodium azide, 0.1% Triton-X-100 and 1% BSA. After incubation at 20°–25° C. for 1 hour, each well was again washed with the wash buffer.

The plate was blotted firmly on an absorbent pad prior to the addition of 100 μl of phenolphthalein monophosphate substrate solution (1.0 g/l phenolphthalein monophosphate (PMP) in 0.5M diethanolamine, pH 8.6 containing 0.02% Bronidox). The plates were incubated at 20°–25° C. for 15 minutes, then hydrolysis of the substrate was stopped by the addition of 100 μl of stop solution (0.4M sodium carbonate, 0.1M 3-(cyclohexylamino)-1-propanesulphonic acid, 0.1M ethylene diaminetetraacetic acid tetrasodium salt, 0.4M sodium hydroxide). Absorbance at 550 nm was measured after the addition of the stop solution.

The results are given in Table 6 below.

TABLE 6

Absorbance at 550 nm of βXIIa Standards and of Human Plasma Samples

| Absorbance at 550 nm | βXIIa Concentration in ng/ml |
|---|---|
| 0.0 0.0 | 0.0 Standard |
| 0.047, 0.050 | 1.0 Standard |
| 0.120, 0.118 | 2.5 Standard |
| 0.264, 0.247 | 5.0 Standard |
| 0.583, 0.556 | 10.0 Standard |
| 1.549, 1.478 | 25.0 Standard |
| 0.347, 0.314 | 6.4, 6.0 Sample |
| 0.245, 0.244 | 4.8, 4.8 Sample |
| 0.387, 0.376 | 7.0, 6.9 Sample |
| 0.364, 0.300 | 6.6, 5.8 Sample |
| 0.330, 0.310 | 6.2, 5.8 Sample |
| 0.437, 0.457 | 7.8, 8.2 Sample |
| 0.140, 0.143 | 2.8, 2.8 Sample |
| 0.179, 0.173 | 3.6, 3.5 Sample |
| 0.454, 0.436 | 8.2, 7.9 Sample |
| 0.316, 0.302 | 6.0, 5.8 Sample |

EXAMPLE 8

Assay using antibodies purified from polyclonal antiserum

The assay was carried out as described in Example 7 except that antibodies obtained from a polyclonal antiserum raised against Factor XII as described in Example 4 and subsequently conjugated to alkaline phosphatase as described in Example 6 were used instead of antibodies 201/9 and 202/16.1.9.

The results are given in Table 7.

TABLE 7

Absorbance at 550 nm

| βXIIa Concentration in ng/ml | Absorbance at 550 nm |
|---|---|
| 0 | 0.048, 0.054 |
| 10 | 0.209, 0.205 |
| 25 | 0.400, 0.396 |
| 50 | 0.564, 0.547 |
| 75 | 0.721, 0.689 |
| 100 | 0.774, 0.777 |
| 125 | 0.823, 0.816 |
| 150 | 0.823, 0.845 |
| 200 | 0.891, 0.911 |

EXAMPLE 9

Assay using a chromogenic substrate

100 μl aliquots of βXIIa standards were added to the wells of microtitre plates that had been coated with monoclonal antibody 2/215 as described in Example 7. The plates were incubated at 20°–25° C. for 1 hour. Each well was then washed with the wash buffer (see Example 7) prior to the addition of 200 μl of chromogenic substrate solution (2 mM β2302 (Kabi Diagnostica, Uxbridge), 65 mM Tris, 135 mM sodium chloride). After incubation for 1 hour at 37° C., 50 μl of 1% acetic acid was added to each well to stop the reaction. The absorbance at 405 nm was measured using a microtitre plate reader.

The results are presented in Table 8.

TABLE 8

Absorbance at 405 nm

| βXIIa Concentration in ng/ml | Absorbance 405 nm |
|---|---|
| 0 | 0.058, 0.057 |
| 10 | 0.077, 0.072 |
| 50 | 0.148, 0.155 |
| 100 | 0.241, 0.226 |
| 150 | 0.275, 0.293 |
| 200 | 0.308, 0.300 |
| 250 | 0.310, 0.306 |

Note: This assay method is not accurate for βXIIa concentrations below about 10 ng/ml, so is not sufficiently sensitive to determine βXIIa in plasma samples. Nevertheless, it is useful for assessing βXIIa at higher concentrations, for example, during isolation and purification and in resulting production batches.

I claim:

1. A monoclonal antibody which binds to Factor βXIIa and to Factor αXIIa, and which shows a corrected cross-reactivity with Factor XII of 0.1% or less, said Factor βXIIa and Factor αXIIa being (i) as produced from Factor XII in vitro, or
  (ii) a form of Factor βXIIa or Factor αXIIa occurring in vivo and obtainable from natural sources, or
  (iii) an analogue of a naturally-occurring Factor βXIIa or Factor αXIIa, which analogue has a modified amino acid sequence, or
  (iv) a synthetic copy or synthetic analogue of a naturally-occurring Factor βXIIa or Factor αXIIa, which copy or analogue has been produced by chemical synthesis or by recombinant DNA technology.

2. A monoclonal antibody as claimed in claim 1 and which is produced by hybridoma cell line 2/215 (ECACC 90011606) or by a subclone thereof.

3. A monoclonal antibody as claimed in claim 1 and which is produced by hybridoma cell line 2/215 (ECACC 90011606) or by a subclone therefor, which antibody has been labeled with a detectable label.

4. A monoclonal antibody as claimed in claim 1, immobilized on a solid support.

5. A hybridoma cell line which produces a monoclonal antibody which binds to Factor βXIIa and to Factor αXIIa, and which shows a corrected cross-reactivity with Factor XII of 0.1% or less, or a subclone thereof.

6. A monoclonal antibody as claimed in claim 1 and which is produced by hybridoma cell line 201/9 (ECACC 90011893) or by a subclone thereof.

7. A monoclonal antibody as claimed in claim 1 and which is produced by hybridoma cell line 201/9 (ECACC 90011893) or by a subclone therefor, which antibody has been labelled with a detectable label.

8. A hybridoma cell line as claimed in claim 5, being cell line 2/215 (ECACC 90011606) or a subclone thereof.

9. A hybridoma cell line as claimed in claim 5, being cell line 201/9 (ECACC 90011893) or a subclone thereof.

10. A kit for carrying out an immunoassay, which kit comprises, each in a separate container or otherwise compartmentalized:
   (i) a monoclonal antibody which binds to Factor βXIIa and to Factor αXIIa, and which shows a corrected cross-reactivity with Factor XII of 0.1% or less, and
   (ii) Factor βXIIa or an antigenic fragment thereof.

11. A kit for carrying out an immunoassay, which kit comprises, each in a separate container or otherwise compartmentalized:
   (a) (i) a monoclonal antibody which binds to Factor βXIIa and to Factor αXIIa, and which shows a corrected cross-reactivity with Factor XII of 0.1% or less, optionally immobilized on a solid support, or
   (ii) Factor βXIIa or an antigenic fragment thereof, or
   (iii) an antibody directed against a monoclonal antibody as defined in (a)(i) above;
   (b)(i) labelled antibody capable of reacting directly or indirectly with Factor βXIIa, or
   (ii) labelled Factor βXIIa, or
   (iii) a chromogenic substrate for Factor βXIIa; and
   (c) a control reagent, which is purified Factor βXIIa or an antigenic fragment thereof.

12. A method for determining the amount of Factor βXIIa in a sample, which comprises:
   (a) incubating said sample with a monoclonal antibody which binds to Factor βXIIa and to Factor αXIIa for a time and under conditions sufficient to allow binding of the antibody to Factor βXIIa, wherein said antibody shows a corrected cross-reactivity with Factor XII of 0.1% or less; and
   (b) determining the amount of Factor βXIIa bound by said antibody.

13. The method as claimed in claim 12, wherein the sample is a sample of plasma obtained from a human subject.

14. A method for determining the amount of Factor XIIa in a sample, which comprises:
   (a) incubating said sample with a monoclonal antibody which binds to Factor βXIIa and to Factor αXIIa for a time and under conditions sufficient to allow binding of the antibody to Factor XIIa, wherein said antibody shows a corrected cross-reactivity with Factor XII of 0.1% or less; and
   (b) determining the amount of Factor XIIa bound by said antibody.

15. The method as claimed in claim 14, wherein the amount of Factor XIIa bound by said antibody is determined by comparing with known amounts of Factor βXIIa bound by said antibody.

16. The method as claimed in claim 14, wherein the sample is a sample of plasma obtained from a human subject.

17. A method for detecting the presence of Factor βXIIa in a sample, which comprises:
   (a) incubating said sample with a monoclonal antibody which binds to Factor βXIIa and to Factor αXIIa for a time and under conditions sufficient to allow binding of the antibody to Factor XIIa, wherein said antibody shows a corrected cross-reactivity with Factor XII of 0.1% or less; and
   (b) detecting the presence of Factor βXIIa bound by said antibody.

18. The method as claimed in claim 17, wherein the sample is a sample of plasma obtained from a human subject.

19. A method for detecting the presence of Factor XIIa in a sample, which comprises:
   (a) incubating said sample with a monoclonal antibody which binds to Factor βXIIa and to Factor αXIIa for a time and under conditions sufficient to allow binding of the antibody to Factor XIIa, wherein said antibody shows a corrected cross-reactivity with Factor XII of 0.1% or less; and
   (b) detecting the presence of Factor XIIa bound by said antibody.

20. A method as claimed in claim 19, wherein the sample is a sample of plasma obtained from a human subject.

* * * * *